(12) United States Patent
Shimada et al.

(10) Patent No.: US 7,658,496 B2
(45) Date of Patent: Feb. 9, 2010

(54) PERIMETER

(75) Inventors: Satoshi Shimada, Hamamatsu (JP); Yoshikatsu Suzumura, Osaka (JP)

(73) Assignee: Kowa Company Ltd. (JP)

( * ) Notice: Subject to any disclaimer, the term of this patent is extended or adjusted under 35 U.S.C. 154(b) by 8 days.

(21) Appl. No.: 11/888,240

(22) Filed: Jul. 31, 2007

(65) Prior Publication Data
US 2008/0036967 A1 Feb. 14, 2008

(30) Foreign Application Priority Data
Aug. 14, 2006 (JP) .............................. 2006-220810

(51) Int. Cl.
*A61B 3/02* (2006.01)
(52) U.S. Cl. ........................ 351/226; 351/224; 351/223; 351/237
(58) Field of Classification Search ................. 351/200, 351/222, 224, 225, 226, 223, 237, 239
See application file for complete search history.

(56) References Cited

U.S. PATENT DOCUMENTS 7,367,674 B2 * 5/2008 Kirchhuebel ................ 351/224

\* cited by examiner

*Primary Examiner*—Jack Dinh
(74) *Attorney, Agent, or Firm*—Adams & Wilks

(57) ABSTRACT

A perimeter performs a kinetic visual field examination on the basis of a response as to whether a subject visually recognizes a displayed stimulus for kinetic visual field examination. The stimulus is displayed a series of times on an inner surface of a visual field dome. An operation is performed in which the subject is made aware of an operating sound of the perimeter while no stimulus is actually displayed. The operation is performed at a predetermined frequency during the display times of the stimulus, and a duration of the operation is determined in accordance with a response time by the subject to the displayed stimulus. The reliability of the kinetic visual field examination is evaluated on the basis of the response of the subject in the performed operation.

12 Claims, 4 Drawing Sheets

PERIMETER

BACKGROUND OF THE INVENTION

1. Field of the Invention

The present invention relates to a perimeter, and more particularly to a perimeter for projecting a stimulus on the inner surface of a visual field dome and for recording the response of a subject relating to a projected position of the stimulus and the visual recognition of the stimulus.

2. Description of the Prior Art

Known in the art is a perimeter for measuring a visual field, in which an illuminated spot is projected as a stimulus on a visual field dome that has a hemispherical projection surface. The projected position of the stimulus is successively varied by an examiner or automatically by the apparatus, and the perimeter records a response of the subject relating to the visual recognition of the stimulus (for example, see Japanese Laid-open Patent Application No. 2002-272685).

In such a perimeter, the position of the stimulus is controlled by a motor, and the stimulus is displayed at a substantially uniform interval, although a certain range of interval variation will be experienced in the examination. Therefore, when the stimulus is displayed, motor sound or other forms of operation sound generated by the perimeter will also be present at a substantially uniform interval. The examiner will accordingly check to see whether the subject is reliably responding by being able to see the stimulus, or is merely responding to the motor sound, and thereby assesses the reliability of the examination results.

For this purposes, with the stimulus not being displayed, only the motor used to display the stimulus is driven at a certain set frequency (e.g., once for every 50 times the stimulus is displayed). If the subject responds in such circumstances, it is assumed that the subject is responding to the motor sound, not because they have seen the stimulus.

A ratio is obtained for the number of times the subject responded when only motor sound was generated. A higher ratio indicates a lower level of examination result reliability. Such a reliability test is referred to as a false-positive test, and is a method traditionally used with perimeters for performing static visual field examinations.

In addition to the false-positive test, another method is used with perimeters for performing static visual field examinations. In this method, the reliability of the examination results is determined by deliberately projecting a stimulus that will definitely be visible to the subject according to the nature of their response during the examination. This reliability test is referred to as a false-negative test. For example, assuming that the sensitivity is measured to be 20 dB at certain viewing conditions (e.g., color and size) at a certain projection position during the examination, a stimulus that is more readily visible than this stimulus is projected at 0 dB (maximum brightness) as a false-negative stimulus at the indicated position. A response is ordinarily expected from the subject in this case. However, in cases where the subject does not respond, it is assumed that they have, e.g., lost the ability to focus, become fatigued, or started to produce inaccurate responses. The following ratio is then provided: (number of non-responses for false-negative stimulus display)/number of times of false-negative stimulus display). A higher ratio indicates lower reliability for an examination result.

The false-positive and false-negative tests described above are static tests wherein the projected stimulus does not move. However, in the visual field examinations performed using a perimeter in, e.g., Japanese Laid-open Patent Application No. 2002-253502, which discloses a kinetic visual field examination, a stimulus projected in a visual field dome is moved in order to provide a kinetic stimulus, and a visual field examination is performed on the basis of the time the subject takes to respond to the moving stimulus. In such examinations as well, it is preferred for a false-positive test or false-negative test to be performed, and the reliability of the kinetic examination results to be evaluated.

It is therefore an object of the present invention to provide a perimeter that is capable of performing a reliable false-positive or false-negative test in a kinetic visual field examination and capable of evaluating the reliability of the kinetic examination results.

SUMMARY OF THE INVENTION

A perimeter according to the present invention performs a visual field examination on the basis of a response as to whether a subject visually recognizes a displayed stimulus. The perimeter comprises means for displaying a stimulus for kinetic examination a plurality of times on an inner surface of a visual field dome and means for performing a first operation and/or a second operation. In the first operation, the subject is made aware of the operating sound of the perimeter while no stimulus is actually displayed. In the second operation, the stimulus is displayed under conditions in which the stimulus is more readily visible than under conditions in which the stimulus is determined to be visible according to previous examination results. The first operation and/or second operation are performed at a predetermined frequency during the plurality of displays of the stimulus for examination. The reliability of the visual field examination is evaluated on the basis of a response of the subject in the first operation and/or the second operation.

In the invention, the displaying of the stimulus for examination, the first operation and/or the second operation are successively performed without any gap therebetween.

In the present invention, a false-positive test and/or a false-negative test can be performed using a simple structure during a kinetic visual field examination. It is therefore possible to satisfactorily evaluate the reliability of the kinetic visual field examination results.

In particular, the stimulus for examination, the false-positive stimulus (false-positive test), and the false-negative stimulus (false-negative test) are all successively displayed without any interval provided therebetween. As a result, less time will be wasted during the entire examination, and a variety of false-positive and false-negative tests can be performed.

Further features of the invention, its nature and various advantages will be more apparent from the accompanying drawings and following detailed description of the invention.

DESCRIPTION OF THE PREFERRED EMBODIMENTS

The present invention will now be described in detail with reference to the embodiments shown in the accompanying drawings.

Figure 1:
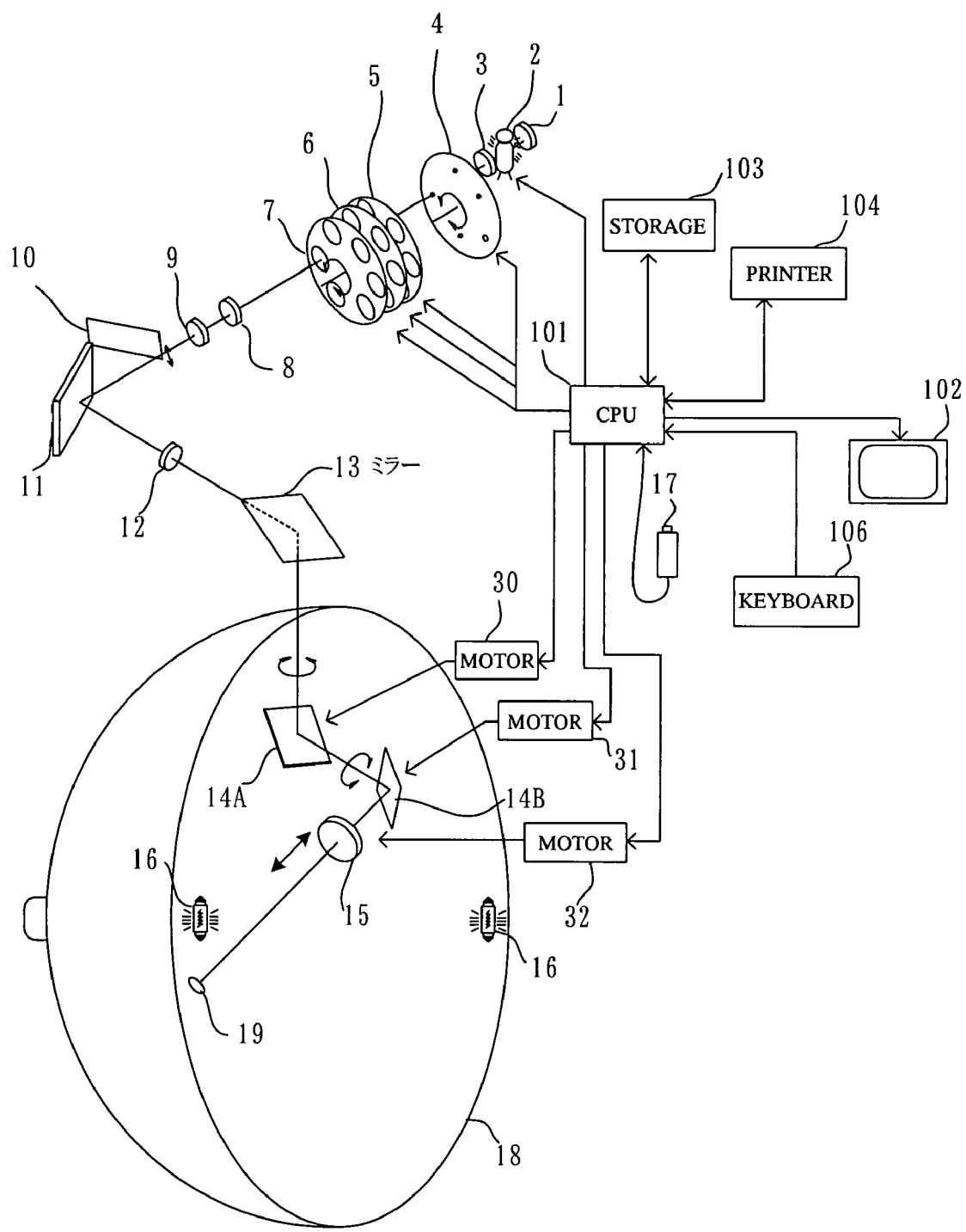
FIG. 1 is an illustrative view showing the arrangement of a perimeter of the present invention.

FIG. 1 shows the structure of a perimeter in which the present invention is employed. In FIG. 1, the numerical symbol 18 indicates a visual field dome. During measurement, the eyes of the subject are aligned using a support frame (not shown) and an alignment mechanism so they will be positioned in the center of the visual field dome 18. Backlight lamps 16, 16 are disposed on an inner part of the visual field dome 18.

The subject watches for a spot-shaped stimulus (stimulus) 19 projected on a projection surface inside the visual field dome 18. When the stimulus is visible, the subject gives a response to an examiner using some suitable method (e.g., operating a response switch 17, or vocally responding).

A projection optical system indicated by the numerical symbols 1 to 15 in FIG. 1 is disposed in order to project and display the stimulus 19. This optical system can be disposed on a projector arm (not shown), for example.

The numerical symbol 2 indicates a stimulus projection lamp as a light source, and a reflection mirror 1 is disposed therebehind. The light of the stimulus projection lamp 2 impinges on a relay lens 8 via a focusing lens 3, a turret disk 4, and filter turrets 5 to 7.

The turret disk 4 sets the size of the stimulus, and is provided with a plurality of openings. A predetermined opening having an appropriate size is moved on the optical axis via a control transmitted from a CPU 101 described hereinafter.

The turret having the numerical symbol 5 is a color filter turret for selecting the color of the stimulus, and turrets 6 and 7 indicates two types of ND filters provided for adjusting light intensity. A light beam passes through the filter turrets 5 to 7, the relay lens 8, and then a focus lens 9 and (the opening of) a shutter 10. The light beam is then reflected by a mirror 11, and then by a mirror 13 via a relay lens 12.

In the present embodiment, two projection mirrors 14A and 14B are provided for controlling the projected position of the stimulus. The rotational positions of the mirrors 14A, 14B are controlled by the CPU 101 via motors 30, 31. The stimulus is thus projected and displayed onto the projection surface of the visual field dome 18 via a projection lens 15. The projector lens 15 is moved along the optical axis by a motor 32 controlled by the CPU 101 in order to focus the projected stimulus 19.

Connected to the CPU 101 via an I/O interface are a monitor 102 comprising a CRT display, an LCD display, or another display device; an external storage device 103 compatible with FD, MO, or other such media; a printer 104; and a keyboard 106 or another such input device.

In this arrangement, the size of the stimulus is set by the turret disk 4 according to a control transmitted from the CPU 101, the color of the stimulus is determined by the color filter turret 5, and the brightness (luminance) of the stimulus is determined by the ND filter turrets 6, 7. A stimulus 19 having a predetermined color, size, and brightness is thereby projected in a predetermined location in the visual field dome 18 via the projection mechanism (1 through 15).

In cases wherein a static examination of the visual field is performed, a stimulus 19 for examination is sequentially displayed (projected) in a plurality of predetermined positions in the visual field dome 18, the subject is made to respond via the response switch 17 when they are able to see the stimulus 19, and the projected positions corresponding to the response made by the subject are recorded. Conversely, in cases wherein a kinetic examination is administered, a stimulus for examination is sequentially displayed in a plurality of predetermined positions in the visual field dome, the displayed stimulus is moved toward the center of the dome in a radial direction at a constant rate (e.g., about 5°/sec), the subject is made to respond via the response switch 17 when they are able to see the moving stimuli, and a record is made of the projected position corresponding to the response made by the subject and the position where the displayed stimulus started to move, or the time elapsed from when the displayed stimulus began moving to when the response was made.

In either the static examination or the kinetic examination, false-positive stimuli and false-negative stimuli are displayed by the CPU 101 and the projection mechanism in the same manner as an ordinary stimulus for examination in order to evaluate the reliability of the examination results. Displaying the false-positive stimulus, as referred to in the present specification, is an operation for a false-positive test (first operation), in which no stimulus for examination is displayed and only the motors 30, 31, 32 for displaying the stimulus, the turret disk 4, and the filter turrets 5 to 7 are driven and operated to generate operating sound. During a plurality of displays of the stimulus for examination, this operation is performed so that the subject can notice the operation sound of the perimeter, but the stimulus is not actually displayed. For purposes of convenience, this operation of the perimeter is referred to as "displaying the false-positive stimulus."

On the other hand, "Displaying the false-negative stimulus" refers to an operation for a false-negative test (second operation), in which, to ensure that the stimulus is definitively recognized by the subject, the stimulus is displayed more brightly at or near the maximum level than when a stimulus for examination was displayed at the time the subject made a response. During a plurality of displays of the stimulus for examination, the stimulus is displayed under conditions in which the stimulus is more readily visible than under conditions in which the stimulus is determined to be visible according to previous examination results.

These false-positive stimuli and false-negative stimuli are displayed at a predetermined frequency (e.g., once every 50 times the stimulus for examination is displayed).

In either a static or kinetic examination, the displaying of the stimulus for examination, the false-positive stimulus, and the false-negative stimulus is carried out in substantially the same manner. The only difference is whether the stimuli are static or kinetic, e.g., whether the stimuli are stationary or moving.

Figure 2:
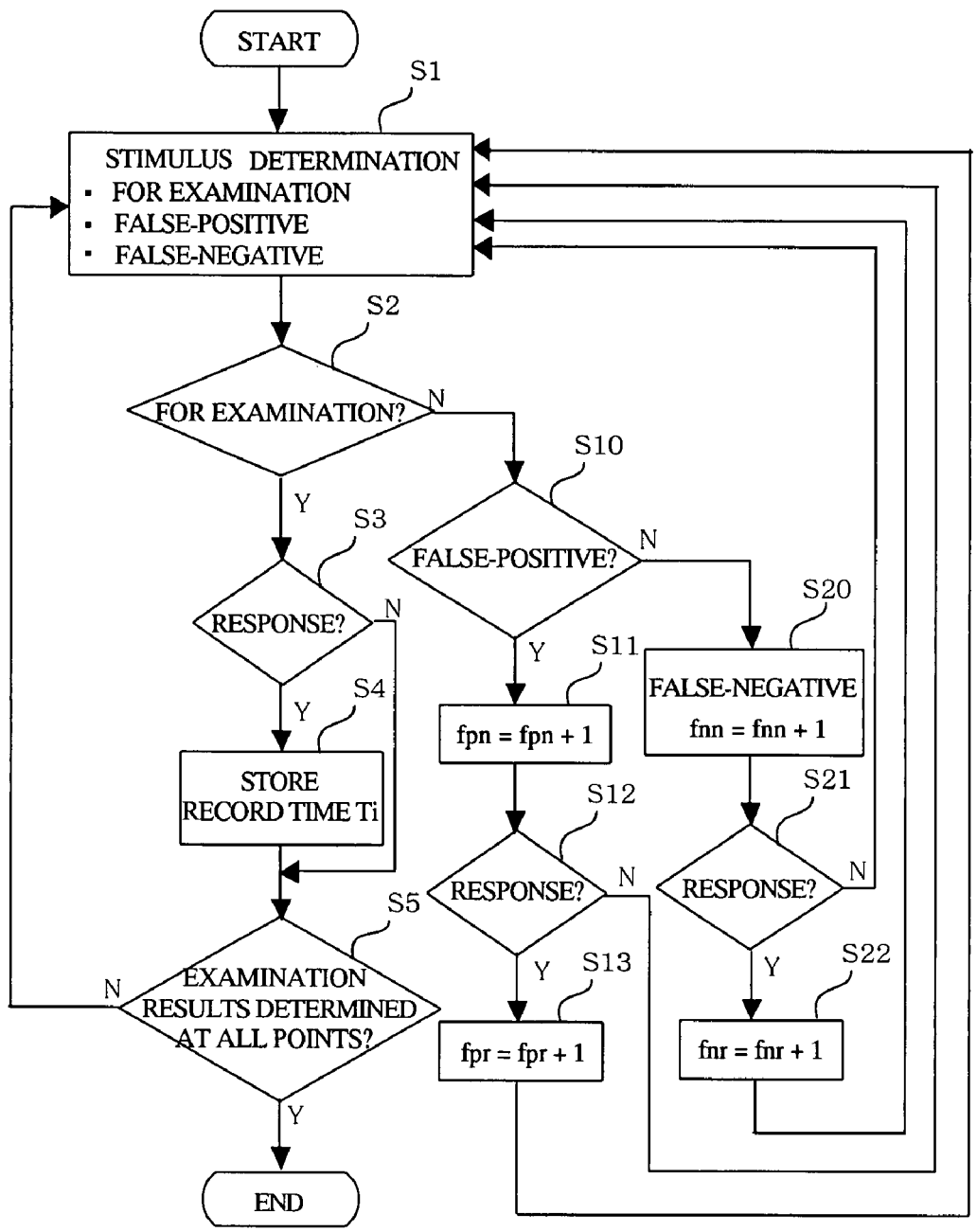
FIG. 2 is a flow chart showing the process flow used when a visual field is measured.

The processes of a kinetic visual field examination and the false-positive and false-negative tests for evaluating the results thereof will be described below with reference to the flow chart shown in FIG. 2.

When the examination begins, the type of stimulus to be displayed is determined in step S1 to be a stimulus for examination, a false-positive stimulus, or a false-negative stimulus. In the case of a stimulus for examination, the stimulus is displayed by the projection mechanism (1 to 15) at predetermined viewing conditions (size, color, and brightness of the stimulus) at a predetermined position in the visual field dome 18, and is moved toward the center of the dome in the radial direction.

The process moves from step S2 to step S3, and the subject responds via the response switch 17 on seeing the moving stimulus. The response time Ti from display to response is then recorded (step S4).

Figure 3A:
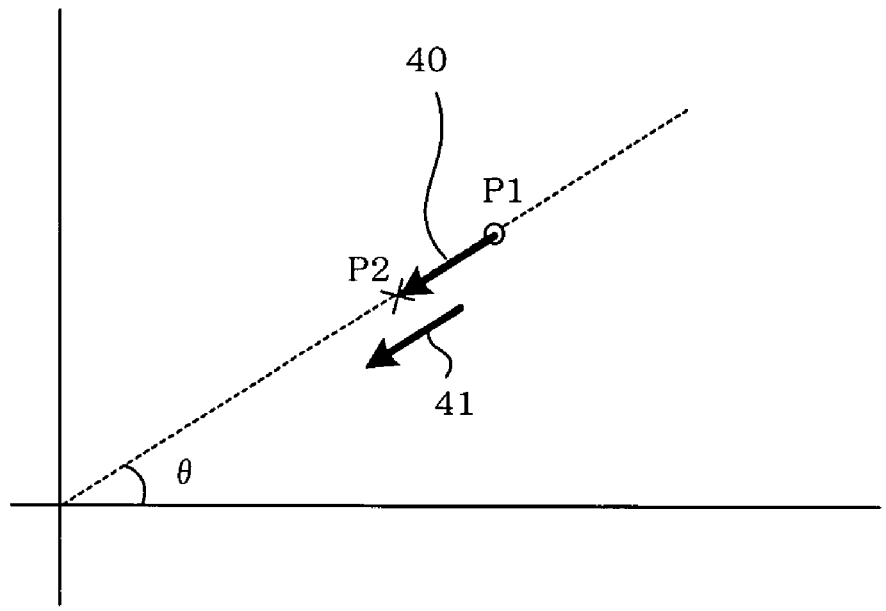
FIG. 3a is a diagram showing an example in which a stimulus for examination is displayed.

FIG. 3a shows an example in which the stimulus 40 for examination is displayed at a position P1 on the meridian θ (the line that extends in the peripheral direction from the center at angle of tilt θ), and the subject has responded when the stimulus has moved to a position P2. In this case, the response time Ti is the time for the stimulus to move from the display-start position P1 to the response position P2.

Next, a decision is made in step S5 as to whether the examination has been carried out at all of the examination points. If not, the process returns to step S1, and the examination is repeated by sequentially varying the stimulus display point (position P1) and the direction of movement according to a program.

While this normal examination is repeated, false-positive stimuli and false-negative stimuli are displayed at a predetermined frequency. The frequency is set to be sufficiently less than the frequency at which the stimuli for examination are displayed so that the total examination time will not be too long. For example, if the stimulus for examination is displayed about 50 times, the false-positive stimulus and the false-negative stimulus will each be displayed about once. In this case, the time t in which the false-positive stimulus and/or false-negative stimulus are displayed will be calculated as t=ΣTi/N+α (constant) based on the response time Ti (i=1 to N). The number of false-positive stimulus displays fpn, number of false-positive stimulus responses fpr, number of false-negative stimulus displays fnn, and number of false-negative stimulus responses fnr are initialized in advance.

FIG. 3a shows a state in which a false-negative stimulus 41 is displayed. In this example, the false-negative stimulus 41 is more readily visible than the stimulus 40 for examination (e.g., the color and size are the same, and the maximum brightness of the perimeter is 0 dB). The stimulus 41 moves toward the center of the dome on the meridian θ slightly away from and past the position P2 over display time t. The stimulus 41 moves on the meridian θ similarly with regard to the stimulus 40, but is shown on a different line in the diagrams for the sake of convenience.

The false-positive stimulus is also projected at the same location and at the time t, although this is not shown in FIG. 3a. With the false-positive stimulus, however, the lamp 2 is turned off, and only the motors 30, 31, 32, the turret disk 4, and the filter turrets 5 to 7 are driven to generate operating sound.

The number of times the false-positive stimulus and false-negative stimulus are displayed is set to a relatively small value in relation to the typical number of times the stimulus for examination is displayed, as described above. The display-position may be either a random position in the case of the false-positive stimulus, or a stimulus position at which a response was previously issued in the case of the false-negative stimulus. In either case, the number of false-positive displays fpn is increased by +1 (step S10, S11) when the false-positive stimulus is displayed, and the number of false-negative displays fnn is increased by +1 (step S10, S20) when the false-negative stimulus is displayed. When the subject responds to the false-positive stimulus, the number of false-positive responses fpr is increased by +1 (step S12, S13). On the other hand, when the subject responds to the false-negative stimulus, the number of false-negative responses fnr is increased by +1 (step S21, S22).

An example of how the false-positive responses and false-negative responses are evaluated shall now be provided.

The false-positive responses are evaluated using the value fpr/fpn, and a higher value indicates lower examination result reliability. The false-negative responses are evaluated using the value (fnn−fnr)/fnn, and a higher value indicates lower examination result reliability.

Figure 3B:
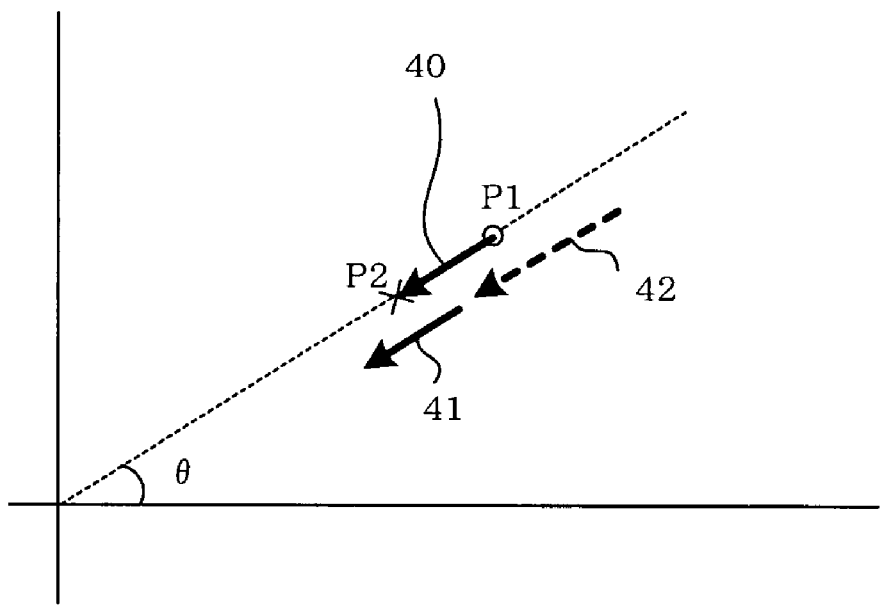
FIG. 3b is a diagram showing an example in which false-positive and false-negative stimuli are displayed.
Figure 4A:
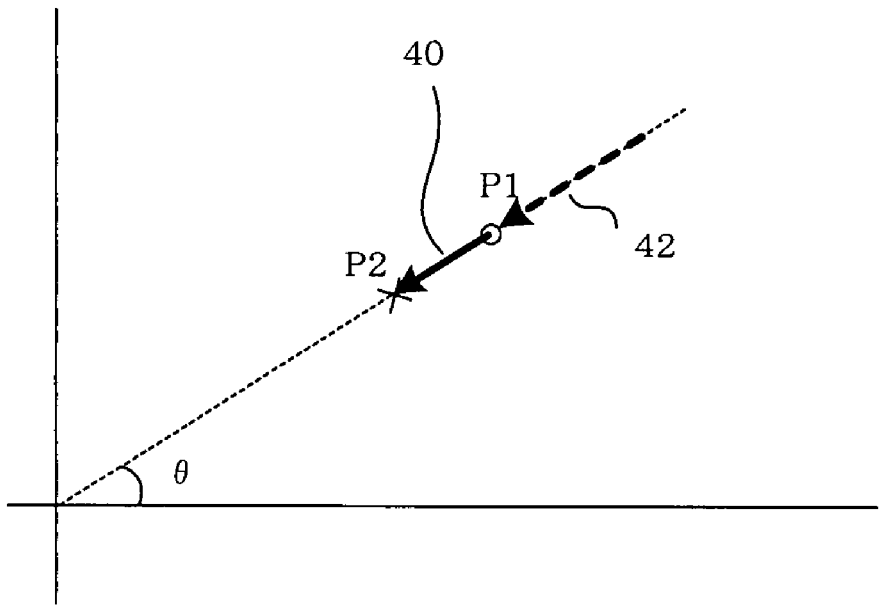
FIG. 4a is a diagram showing still another example in which a false-positive stimulus and a stimulus for examination are displayed.
Figure 4B:
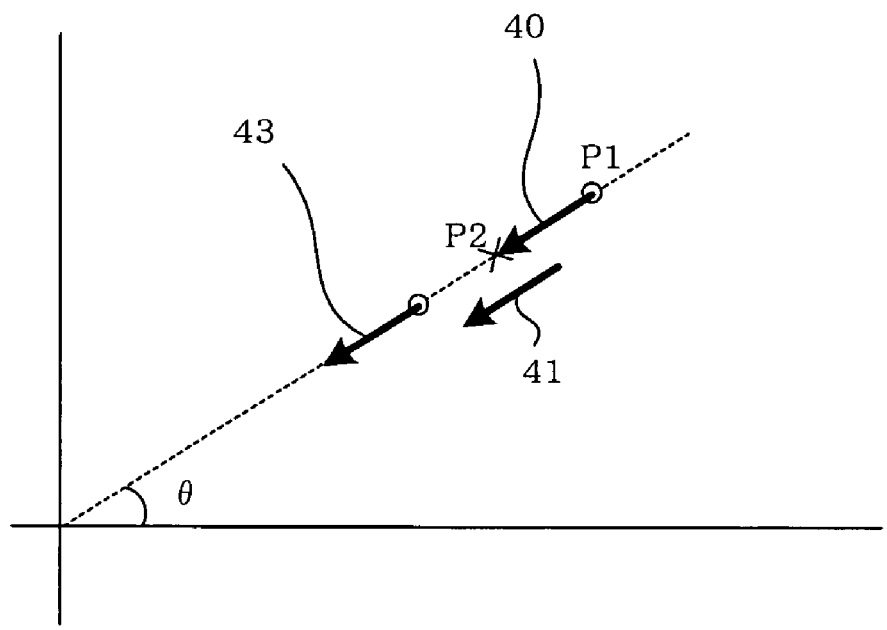
FIG. 4b is a diagram showing still another example in which a stimulus for examination and false-positive and false-negative stimuli are displayed.

FIGS. 3b, 4a, and 4b show examples in which a variety of stimuli are displayed.

FIG. 3b shows an example in which a false-positive stimulus 42 is displayed prior to the false-negative stimulus 41 displayed in FIG. 3a. In this example, the false-negative stimulus 41 is displayed in succession relative to the false-positive stimulus 42.

In FIG. 4a, the stimulus 40 for examination is displayed in succession relative to the false-positive stimulus 42 without any gap being provided between displays.

In FIG. 4b, another stimulus 43 for examination is displayed in succession relative to the false-negative stimulus 41 that has been displayed after the stimulus 40 for examination. In this example, no gap is also provided among the displays.

In examples other than those described above, it is also possible for the continuous stimulus display to be performed using any two stimuli selected from the false-negative stimulus, the false-positive stimulus, and the stimulus for examination. It is also possible for the continuous stimulus display to be performed using all three of these stimuli.

The stimuli are thus displayed in succession without any gap being provided. This allows the examination time to be reduced and a variety of false-positive and false negative tests to be performed.

Both false-positive and false-negative tests were performed in the embodiments described above, but the results of the kinetic visual field examination may be evaluated by either of these tests.

The results and evaluation of the visual field examination described above are graphically displayed on the monitor 102 according to the examination method, outputted to the printer 104, or stored and saved on the external memory device 103, which is compatible with FD, MO, or another media format.

What is claimed is:

1. A perimeter for performing a kinetic visual field examination on the basis of a response as to whether a subject visually recognizes a displayed stimulus for kinetic visual field examination, the perimeter comprising:

means for displaying the stimulus a plurality of times on an inner surface of a visual field dome;

means for performing an operation in which the subject is made aware of an operating sound of the perimeter while no stimulus is actually displayed, the operation being performed at a predetermined frequency during the plurality of displays of the stimulus, and a duration of the operation being determined in accordance with a response time by the subject to the displayed stimulus; and means for evaluating the reliability of the kinetic visual field examination on the basis of the response of the subject in the performed operation.

2. A perimeter as set forth in claim 1; wherein the operation and the display of the stimulus are successively performed without any interval therebetween.

3. A perimeter as set forth in claim 1; further comprising means for moving the stimulus at a constant speed on a meridian toward a center of the visual field dome.

4. A perimeter for performing a kinetic visual field examination on the basis of a response as to whether a subject visually recognizes a displayed stimulus for kinetic visual field examination, the perimeter comprising:

means for displaying the stimulus a plurality of times on an inner surface of a visual field dome;

means for performing an operation in which the stimulus is displayed under conditions in which the stimulus is more readily visible than under conditions in which the stimulus is determined to be visible according to previous examination results, the operation being performed at a predetermined frequency during the plurality of displays of the stimulus, and a duration of the operation being determined in accordance with a response time by the subject to the displayed stimulus; and means for evaluating the reliability of the kinetic visual field examination on the basis of the response of the subject in the performed operation.

5. A perimeter as set forth in claim 4; wherein the operation and the display of the stimulus are successively performed without any interval therebetween.

6. A perimeter as set forth in claim 4; further comprising means for moving the stimulus at a constant speed on a meridian toward a center of the visual field dome.

7. A perimeter for performing a kinetic visual field examination on the basis of a response as to whether a subject visually recognizes a displayed stimulus for kinetic visual field examination, the perimeter comprising:

means for displaying the stimulus a plurality of times on an inner surface of a visual field dome;

means for performing a first operation in which the subject is made aware of an operating sound of the perimeter while no stimulus is actually displayed, the first operation being performed at a predetermined frequency during the plurality of displays of the stimulus, and a duration of the first operation being determined in accordance with a response time by the subject to the displayed stimulus;

means for performing a second operation in which the stimulus is displayed under conditions in which the stimulus is more readily visible than under conditions in which the stimulus is determined to be visible according to previous examination results, the second operation being performed at a predetermined frequency during the plurality of displays of the stimulus, and a duration of the second operation being determined in accordance with a response time by the subject to the displayed stimulus; and means for evaluating the reliability of the visual field examination on the basis of the response of the subject in the first and second operations.

8. A perimeter as set forth in claim 7; wherein the first and second operations and the display of the stimulus are successively performed without any interval therebetween.

9. A perimeter as set forth in claim 7; further comprising means for moving the stimulus at a constant speed on a meridian toward a center of the visual field dome.

10. A perimeter for performing a kinetic visual field examination on the basis of a response as to whether a subject visually recognizes a displayed stimulus for kinetic visual field examination, the perimeter comprising:

means for displaying the stimulus a plurality of times on an inner surface of a visual field dome;

means for performing at least one of a first operation and a second operation, the first operation being an operation in which the subject is made aware of an operating sound of the perimeter while no stimulus is actually displayed, the second operation being an operation in which the stimulus is displayed under conditions in which the stimulus is more readily visible than under conditions in which the stimulus is determined to be visible according to previous examination results, the at least one of the first and second operations being performed at a predetermined frequency during the plurality of displays of the stimulus, the display of the stimulus and the at least one of the first and second operations being successively performed without any interval therebetween; and means for evaluating the reliability of the visual field examination on the basis of the response of the subject to the performed at least one of the first and second operations.

11. A perimeter as set forth in claim 10; wherein the means for performing performs both the first operation and the second operation, the display of the stimulus and the first and second operations being successively performed without any intervals therebetween; and wherein the means for evaluating evaluates the reliability of the visual field examination on the basis of the response of the subject to the performed first and second operations.

12. A perimeter as set forth in claim 10; further comprising means for moving the stimulus at a constant speed on a meridian toward a center of the visual field dome.

* * * * *